United States Patent
Takimoto et al.

(10) Patent No.: US 9,029,606 B2
(45) Date of Patent: May 12, 2015

(54) METHOD FOR PRODUCING 2-CHLOROMETHYLBENZALDEHYDE, 2-CHLOROMETHYLBENZALDEHYDE-CONTAINING COMPOSITION, AND METHOD FOR STORING SAME

(75) Inventors: Masashi Takimoto, Shizuoka (JP); Tomonori Yamaoka, Shizuoka (JP); Yoshio Onogawa, Shizuoka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/128,239

(22) PCT Filed: Jun. 27, 2012

(86) PCT No.: PCT/JP2012/066402
§ 371 (c)(1),
(2), (4) Date: Mar. 13, 2014

(87) PCT Pub. No.: WO2013/002265
PCT Pub. Date: Jan. 3, 2013

(65) Prior Publication Data
US 2014/0187822 A1    Jul. 3, 2014

(30) Foreign Application Priority Data

Jun. 27, 2011   (JP) ................................. 2011-141552

(51) Int. Cl.
*C07C 45/42*   (2006.01)
*C07C 45/43*   (2006.01)
*C07C 47/55*   (2006.01)

(52) U.S. Cl.
CPC .................. *C07C 45/42* (2013.01); *C07C 45/43* (2013.01); *C07C 47/55* (2013.01)

(58) Field of Classification Search
CPC ....................................................... C07C 45/43
USPC ................................................ 568/421, 437
See application file for complete search history.

(56) References Cited

U.S. PATENT DOCUMENTS

| | | |
|---|---|---|
| 3,499,934 A | 3/1970 | Pyne |
| 4,439,620 A | 3/1984 | Klauke et al. |
| 4,914,127 A | 4/1990 | Beck et al. |
| 5,278,152 A | 1/1994 | Peyman et al. |

FOREIGN PATENT DOCUMENTS

| | | |
|---|---|---|
| CA | 2032772 C | 10/2001 |
| EP | 0555698 A1 | 8/1993 |
| JP | 39-11367 B1 | 6/1964 |
| JP | 62-51641 A | 3/1987 |
| JP | 6-16685 A | 1/1994 |
| JP | 08092148 A | 4/1996 |
| JP | 2006-335737 A | 12/2006 |
| JP | 2007046142 A | 2/2007 |
| JP | 2007119863 A | 5/2007 |

OTHER PUBLICATIONS

International Preliminary Report on Patentability and Written Opinion issued Jan. 7, 2014 in International Application No. PCT/JP2012/066402.
Nadeem Iqbal, et al., "Synthesis and Calcium Channel Modulation Effects of Isopropyl 1,4-Dihydro-2,6-dimethyl-3-nitro-4-phenylpyridine-5-carboxylates Possessing Ortho-, Meta-, and Para-$CH_2S(O)nMe$ and -$S(O)nMe$ (n=0-2) Phenyl Substituents", Drug Development Research, 2000, vol. 51, No. 3, pp. 177-186.
Klaus Banert, et al., "Elusive ethynyl azides: trapping by 1,3-dipolar cycloaddition and decomposition to cyanocarbenes", Chemical Communications (Cambridge, United Kingdom), vol. 46, No. 23, 2010, pp. 4058-4060, compound 24.
First Office Action issued Oct. 9, 2014 in counterpart Chinese Patent Application No. 201280032170.7 with English translation.
Oppenheim, A., XP002734657, "Uber die Einwirkung von Schwefelsaure auf mehrfach gechlorte Kohlenwasserstoffe", Berichte Der Deutschen Chemischen Gesellschaft, vol. 2, No. 1, 1869, pp. 212-214.
Supplementary European Search Report dated Feb. 18, 2015, issued in counterpart EP Application No. 12803767.8.

*Primary Examiner* — Sikarl Witherspoon
(74) *Attorney, Agent, or Firm* — Sughrue Mion, PLLC

(57) ABSTRACT

A process for obtaining an industrially useful 2-chloromethylbenzaldehyde-containing liquid composition at a high yield is provided. More specifically, a process for producing 2-chloromethylbenzaldehyde comprising step (A) of mixing 1-dichloromethyl-2-chloromethylbenzene and sulfuric acid having a concentration of 84.5% by weight or more; and step (B) of mixing a mixture obtained in step (A) and water is provided.

10 Claims, No Drawings

METHOD FOR PRODUCING 2-CHLOROMETHYLBENZALDEHYDE, 2-CHLOROMETHYLBENZALDEHYDE-CONTAINING COMPOSITION, AND METHOD FOR STORING SAME

CROSS REFERENCE TO RELATED APPLICATIONS

This application is a National Stage of International Application No. PCT/JP2012/066402 filed Jun. 27, 2012, claiming priority based on Japanese Patent Application No. 2011-141552 filed Jun. 27, 2011, the contents of all of which are incorporated herein by reference in their entirety.

TECHNICAL FIELD

The present invention relates to a process for producing 2-chloromethylbenzaldehyde, a 2-chloromethylbenzaldehyde-containing composition and a method for storing the same.

BACKGROUND ART

2-Chloromethylbenzaldehyde (hereinafter, referred to as 2CMAD in some cases) is useful as an intermediate of medicaments and electronic materials (JP 2006-335737 A, JP 6-016685 A and JP 62-051641 A). However, a specific process for producing it, physical properties thereof and the like are not disclosed in detail.

Solely, JP 2006-335737 A discloses that 2CMAD can be produced by hydrolysis of 1-dichloromethyl-2-chloromethylbenzene (hereinafter, referred to as TCOX in some cases), but a detailed hydrolysis condition is unknown.

By reference to a hydrolysis condition of similar compounds, the present inventors studies in detail and, as a result, confirmed that even when TCOX and water are reacted in line with the scheme described in JP 2006-335737 A, 2CMAD is not obtained at a good yield only by the reaction, and there is the technical problem which should be addressed. In addition, the present inventors knew that the thus obtained 2CMAD has not necessarily sufficiently satisfactory stability at room temperature, and stability in a reaction using it as a raw material is not also necessarily sufficiently satisfactory. Even when an objective substance is obtained at an intermediary yield in a small scale and short time reaction in an laboratory in Examples of JP 2006-335737 A, JP 6-016685 A and JP 62-051641 A, in the case where large scale synthesis at an industrial scale is envisioned, it becomes difficult to use the objective substance as an industrial raw material, if a yield is reduced, and the objective substance is degraded during storage.

SUMMARY OF INVENTION

The present inventors intensively studied, and reached the present invention. That is, the present invention is as follows:

[1] A process for producing 2-chloromethylbenzaldehyde comprising:
step (A) of mixing 1-dichloromethyl-2-chloromethylbenzene and sulfuric acid having a concentration of 84.5% by weight or more; and
step (B) of mixing a mixture obtained in step (A) and water.

[2] The process according to [1], comprising step of neutralizing an organic phase of the mixture obtained in step (B).

[3] The process according to [1] or [2], further comprising a step of mixing the resulting 2-chloromethylbenzaldehyde with at least one selected from the group consisting of a polymerization inhibitor and an antioxidant.

[4] The process according to [3], wherein the at least one selected from the group consisting of a polymerization inhibitor and an antioxidant is at least one selected from the group consisting of 2,6-bis(1,1-dimethylethyl)-4-methylphenol (BHT), hydroquinone, monomethyl hydroquinone and phenothiazine.

[5] The process according to any one of [1] to [4], wherein sulfuric acid having a concentration of 84.5% by weight or more in step (A) contains water at 0.4 mol or more based on 1 mol of 1-dichloromethyl-2-chloromethylbenzene.

[6] A composition comprising 2-chloromethylbenzaldehyde and at last one selected from the group consisting of a polymerization inhibitor and an antioxidant.

[7] The composition according to [6], wherein the at least one selected from the group consisting of a polymerization inhibitor and an antioxidant is at least one selected from the group consisting of 2,6-bis(1,1-dimethylethyl)-4-methylphenol (BHT), hydroquinone, monomethyl hydroquinone and phenothiazine.

[8] The composition according to [6] or [7], further comprising 1-dichloromethyl-2-chloromethylbenzene, wherein a content ratio of a molar quantity of 2-chloromethylbenzaldehyde [$M_{2CMAD}$] defined by the relationship with a molar quantity of 1-dichloromethyl-2-chloromethylbenzene [$M_{TCOX}$] ($[\eta_{2CMAD}]=[M_{2CMAD}]/([M_{2CMAD}]+[M_{TCOX}])$) is 95% or more.

[9] A method for storing a composition comprising storing the composition as defined in any one of [6] to [8] under nitrogen atmosphere.

According to the process of the present invention, 2-chloromethylbenzaldehyde can be produced at an excellent yield also in implementation at industrial scale. Further, according to the present invention, a 2-chloromethylbenzaldehyde-containing composition excellent in stability and a method for storing the same can be provided.

DESCRIPTION OF EMBODIMENT

The present invention will be explained in detail below based on preferable aspects thereof.

(First Aspect)

A process for producing 2-chloromethylbenzaldehyde (2CMAD) in the present aspect comprises step (A) of mixing 1-dichloromethyl-2-chloromethylbenzene (TCOX) and 84.5% by weight or more of sulfuric acid; and step (B) of mixing a mixture obtained in step (A) and water. By performing step (A) and step (B), TCOX is converted into 2CMAD at a high conversion ratio. Hereinafter, a reaction of converting TCOX into 2CMAD is referred to as "hydrolysis reaction" or "hydrolysis" in some cases.

Sulfuric acid used in step (A) is an aqueous solution of $H_2SO_4$, and its concentration is 84.5% by weight or more, and preferably 96% or less. Further, a concentration of sulfuric acid is preferably 85% by weight or more, and more preferably 90% by weight or more. An amount of sulfuric acid is preferably 1 mol or more, and more preferably 2 mol or more based on 1 mol of TCOX. There is no upper limit of an amount of sulfuric acid, but 4 mol or less based on 1 mol of TCOX is practical. When an amount of sulfuric acid is 1 mol or more based on 1 mol of TCOX, it does not take too much time for completing a reaction between TCOX and 84.5% by weight or more of sulfuric acid, and this is preferable.

The reaction temperature in step (A) is not particularly limited, but at the temperature of 15° C. or higher, a reaction rate is sufficiently maintained, and such temperature is preferable. This reaction temperature is preferably 25° C. or lower, in respect of stability of generated 2CMAD. The reaction time is not particularly limited, but in view of the range practical in industrial production, 15 hours or shorter is preferable, and 8 hours or shorter is more preferable. There is particularly no lower limit, but 3 hours or longer is practical.

A method of carrying out the step of (A) is not limited, but usually, the method is performed by a method of adding dropwise 1-dichloromethyl-2-chloromethylbenzene into sulfuric acid having the aforementioned concentration. Since an induction phase is seen in a reaction initial stage, a method of adding dropwise a part of 1-dichloromethyl-2-chloromethylbenzene, confirming that a reaction between TCOX and 84.5% by weight or more of sulfuric acid is initiated and, thereafter, adding remaining 1-dichloromethyl-2-chloromethylbenzene can be also adopted. When a concentration of sulfuric acid is lower than 84.5% by weight, the reaction is not completed. As 1-dichloromethyl-2-chloromethylbenzene used in a raw material, for example, 1-dichloromethyl-2-chloromethylbenzene produced by photochlorination of orthoxylene can be used by distillation.

In the present aspect, even when sulfuric acid used in step (A) contains water at less than 1 mol based on 1 mol of TCOX, a hydrolysis reaction can be completed by mixing a mixture obtained in step (A) and water, in step (B) described later. That is, the hydrolysis reaction may progress in step (A), or may be completed via step (B). Sulfuric acid used in step (A) contains preferably water at 0.4 mol or more, contains more preferably water at 0.8 mol or more, contains further preferably water at 1 mol or more based on 1 mol of TCOX. There is particularly no upper limit of an amount of water contained in sulfuric acid, but 2 mol or less based on 1 mol of TCOX is practical.

The mixture obtained in step (A) is present in a state where the materials are uniformly mixed in a reaction liquid, and by performing step (B) of mixing the mixture and water, 2CMAD can be obtained, or an organic compound component containing 2CMAD can be fractionated and, thereby, the reaction liquid can be separated into the organic compound component, and water and components dissolved therein. Herein, in the organic compound component, 1-dichloromethyl-2-chloromethylbenzene (TCOX) which is a raw material compound and 2-chloromethylbenzaldehyde (2CMAD) which is a product are present together in some cases. Since separation of both organic compound components is not usually easy, and 2CMAD is an easily degradable compound, it is not practical to perform purification treatment by heating or the like. In other words, it is extremely important to obtain 2CMAD at a high yield, at the stage of a reaction of producing 2CMAD.

In the present invention, unless otherwise noted, "water" is used in a sense that water and an aqueous medium (an aqueous solution in which a substance soluble in water is dissolved in water) are included.

It is preferable to add water used in step (B) at such an amount that a concentration of sulfuric acid becomes 70% by weight or less, in a point that liquid separation is performed well, and 2CMAD is isolated. There is no upper limit of a use amount of water, but use of more water than necessary becomes disadvantageous in economic efficiency. The temperature at which water is added is preferably 30° C. or lower in view of stability of a product, and in view of a solidifying point of water, the temperature which is lower between 5° C. or higher and 30° C. or lower is further preferable. The temperature at which a concentration of sulfuric acid becomes 70% by weight or less, and the organic layer and the aqueous layer are separated, is preferably 15° C. to 30° C. in respect of liquid separability.

As described above, 2CMAD obtained at a high yield means that an amount of TCOX which is a raw material compound is small. According to the present aspect, since a yield of 2CMAD is high, 2CMAD having a high concentration can be provided for subsequent synthesis of a desired chemical product. In the present embodiment, it is preferable that this 2CMAD concentration $[\eta_{2CMAD}]$, that is, a ratio of the molar quantity of 2CMAD $[M_{2CMAD}]$ relative to a total amount of the molar quantity of TCOX $[M_{2TCOX}]$ and the molar quantity of 2CMAD $[M_{2CMAD}]$, $[\eta_{2CMAD}]=[M_{2CMAD}]/([M_{2CMAD}]+[M_{TCOX}])$ is high. A concentration of 2CMAD $[\eta_{2CMAD}]$ is preferably 95% or more, more preferably 98% or more. There is particularly no upper limit, but for example, in view of extension of the reaction time, it is also possible to define a concentration as 100% or less. By obtaining 2CMAD having a high concentration like this, a raw material having good quality in which an amount of TCOX is suppressed small can be obtained, and the advantage thereof is further exerted by stabilization described later. A concentration of 2CMAD is preferably 95% or more, and more preferably stabilized in the range of 95 to 99%.

(Second Aspect)

It is preferable to perform separation into two layers of the organic phase and the aqueous phase by performing step (A) and step (B) in the first aspect, as described above. Thereupon, a liquid separation operation is performed, the fractionated organic phase is usually washed with water, a pH of the solution (organic phase) exhibits strong acidity, and the organic phase does not stand long term preservation, in some cases. This is because 2-chloromethylbenzaldehyde considerably easily undergoes oxidation, and is easily changed into phthalide under the acidic condition. This made it difficult to handle 2-chloromethylbenzaldehyde at an industrially large amount. The present inventors found out that stability of 2-chloromethylbenzaldehyde is improved by performing step of mixing 2-chloromethylbenzaldehyde and at least one selected from the group consisting of a polymerization inhibitor and an antioxidant (hereinafter, referred to as stabilizer in some cases). This enabled to store 2-chloromethylbenzaldehyde under the usual production time (e.g. around 2 days), and enabled to use 2-chloromethylbenzaldehyde as a raw material in a next step at a large amount. Examples of the stabilizer include 2,6-bis(1,1-dimethylethyl)-4-methylphenol (hereinafter, referred to as BHT in some cases), hydroquinone, monomethyl hydroquinone, phenothiazine, methanol, Quino Power (registered trademark), $MnCl_2$, $CuCl_2$ and TEMPO, at least one selected from the group consisting of 2,6-bis(1,1-dimethylethyl)-4-methylphenol (BHT), hydroquinone, monomethyl hydroquinone and phenothiazine is preferable, phenothiazine and BHT are more preferable, and BHT is further preferable. A use amount of the stabilizer is preferably 50 to 500 ppm (stabilizer/2CMAD), and more preferably 100 to 200 ppm relative to 2CMAD on weight basis. When a use amount is less than 50 ppm, or when a use amount is more than 500 ppm, stability of 2-chloromethylbenzaldehyde is not improved as compared with stability of 2CMAD not mixed with the stabilizer, in some cases. Particularly, since excessively much addition rather causes increase in impurities, it is preferable that an addition amount does not become such an amount.

It was observed that a self degradation reaction of 2CMAD produces phthalide by oxidation with oxygen in the air. Therefore, it is preferable to perform storage and a reaction under nitrogen atmosphere.

(Third Aspect)

Stabilization treatment by neutralizing a mixed liquid containing 2CMAD, which is a third aspect of the present invention, will be explained. Specifically, examples include an operation of performing neutralization by mixing a mixed liquid containing 2CMAD obtained via step (A) and step (B), and an aqueous alkaline solution (preferably, an aqueous solution containing an alkali buffer). Thereupon, it is preferable to measure a pH of a mixed liquid of the organic phase containing 2CMAD and the aqueous phase, and adjusting a pH of the mixed liquid at 6 to 8.

Thereupon, the kind of the alkali to be added to water is not limited, but disodium hydrogen phosphate is more preferable. Disodium hydrogen phosphate has a buffering effect, and can retain a pH even when a use amount is changed to some extents. When the alkali such as an aqueous sodium hydroxide solution is used, considerable labor is required for strictly controlling the liquid at a pH of 6 to 8 by mixing with 2CMAD in some cases, and it is preferable to use an adjusting agent having the aforementioned buffering effect. Further, by adding the stabilizer shown above, long term preserving property can be further enhanced. In addition, in the present invention, a pH refers to a value measured by the method shown in Examples unless otherwise noted.

As described above, according to a preferable aspect of the present invention, 1-dichloromethyl-2-chloromethylbenzene (TCOX) is hydrolyzed under room temperature, and is converted into 2-chloromethylbenzaldehyde (2CMAD) at a good yield and a good purity (first aspect). A preferable range of a concentration of 2-chloromethylbenzaldehyde produced thereupon [$\eta_{2CMAD}$] was described above. Further, according to the second aspect and the third aspect, 2-chloromethylbenzaldehyde can be subjected to a reaction of a next step without degradation during preservation under the usual production time (e.g. around 2 days).

When 2CMAD is not obtained at a high yield in the reaction, it is troublesome to separate TCOX which remains unreacted, and it is a great industrial advantage that 2CMAD having a high concentration is directly obtained. As described above, 2CMAD is degradable. For this reason, an aspect of performing stabilization treatment via an operation under non-heating mild condition of addition of water and separation has great meaningfulness. Such aspect realizes large scale production of a high quality raw material composition containing 2CMAD and, further, contributes to reduction in consumption energy.

Specifically, 2-chloromethylbenzaldehyde which is not subjected to treatment shown in the second aspect and the third aspect, even when 2CMAD having a high concentration is obtained by the first aspect, reduces the purity by around 20% by an autoxidation reaction in 48 hours in preservation at room temperature. This means that a reaction of a next step using 2-chloromethylbenzaldehyde as an intermediate raw material must be immediately carried out without a time lag, and this is considerably disadvantageous in industrial production. It is shown that, when time adjustment in the reaction field, and preservation of an intermediate by trouble are compelled, further reduction in the purity occurs. As a response thereto, a method of inhibiting an autoxidation reaction under nitrogen atmosphere is effective. However, complete air shut-out at industrial scale and storage under nitrogen atmosphere require a special facility response, and the risk that air enters should be considered. Also when there is unavoidable contact with air like this, the second aspect and the third aspect are effective. According to the present aspect, 2-chloromethylbenzaldehyde can be subjected to a reaction of a next step without degradation even during long term preservation below room temperature.

The 2-chloromethylbenzaldehyde-containing composition obtained as described above can be used as a raw material of industrial materials such as agrochemicals, medicaments and porphyrin, and by using the present composition, a production route of a shorter step than the previous method can be realized in some cases. According to the present invention, since 2CMAD in the aforementioned liquid composition can be obtained at a high concentration, and preferably stably, as described above, it enables to produce the aforementioned chemical products at high quality and inexpensive cost.

EXAMPLES

The present invention will be explained in more detail below by way of examples, but the present invention is not restrictively construed by them.

Example 1

Influence of a concentration of sulfuric acid on hydrolysis of 1-dichloromethyl-2-chloromethylbenzene Sulfuric acid having a concentration of 96% by weight was optionally diluted with water to prepare sulfuric acid having a concentration described in the following Table 1. 1-Dichloromethyl-2-chloromethylbenzene was added thereto, and the mixture was stirred for the predetermined time while retaining the temperature of 15 to 25° C. Thereafter, the mixture was diluted with water having a 0.5-fold weight (about a 0.4-fold amount by volume) (relative to TCOX). The diluted mixed liquid was separated into the organic phase and the aqueous phase, and this organic phase was fractionated to obtain an objective liquid composition. The result of analysis of the liquid composition constituting this organic phase by gas chromatography is shown below. In the following Table 1, a content ratio of 2CMAD [$\eta_{2CMAD}$] in the resulting liquid composition can be assessed by a ratio obtained by dividing a production amount % of 2CMAD [$\%_{2CMAD}$] by a sum of a remaining ratio % of raw material TCOX [$\%_{TCOX}$] and a production amount % of 2CMAD [$\%_{2CMAD}$]([$\%_{2CMAD}$]/([$\%_{2CMAD}$]+[$\%_{TCOX}$])).

TABLE 1

| Sulfuric acid concentration % | Mol ratio of sulfuric acid relative to TCOX | Mol ratio of water relative to TCOX | Reaction time | Remaining amount of raw material TCOX % | Production amount of 2CMAD % | Remark |
|---|---|---|---|---|---|---|
| 96.0 | 2.05 | 0.47 | 5 hours | 0 | 99.1 | Example 1-1 |
| 96.0 | 4.10 | 0.93 | 3 hours | 0.1 | 99.3 | Example 1-2 |
| 89.5 | 2.46 | 1.56 | 5 hours | 0.5 | 93.6 | Example 1-3 |
| 84.9 | 2.05 | 1.97 | 15 hours | 0.4 | 98.7 | Example 1-4 |
| 85.0 | 1.05 | 1.01 | 37 hours | 4.4 | 93.9 | Example 1-5 |

TABLE 1-continued

| Sulfuric acid concentration % | Mol ratio of sulfuric acid relative to TCOX | Mol ratio of water relative to TCOX | Reaction time | Remaining amount of raw material TCOX % | Production amount of 2CMAD % | Remark |
|---|---|---|---|---|---|---|
| 81.8 | 2.05 | 2.47 | 23 hours | 47.5 | 51.0 | Comparative Example 1-1 |
| 78.9 | 2.46 | 3.56 | 5 hours | 95.9 | 2.0 | Comparative Example 1-2 |
| 96.0 | 1.03 | 0.23 | 22 hours | 45.2 | 53.7 | Reference Comparative Example |

TCOX: 1-dichloromethyl-2-chloromethylbenzene
2CMAD: 2-chloromethylbenzaldehyde

From the above result, it is seen that, according to the present invention, 2CMAD can be obtained at a high yield, and the 2CMAD-containing liquid composition having a high concentration can be obtained, using TCOX as a raw material (see Examples 1-1 to 1-5). In addition, it is shown that, even when an absolute amount of water relative to TCOX is deficient for hydrolysis, in the case where a sulfuric acid concentration is high, hydrolysis progresses immediately when diluted with water after the predetermined reaction time (see Example 1-1). Conversely, it is seen that, even when an absolute amount of water is sufficient, in the case where a sulfuric acid concentration is too small, TCOX remains without being hydrolyzed, at any of the reaction and the post-treatment (see Comparative Examples 1-1 and 1-2).

Example 2

Step of Synthesizing 2-chloromethylbenzaldehyde

A 500 mL flask was charged with 146.1 g (1.43 mol) of sulfuric acid having a concentration of 96% by weight and 9.9 g (0.55 mol) of water, the temperature was cooled to 25° C., 115.2 g (0.55 mol) of 1-dichloromethyl-2-chloromethylbenzene was added, and the mixture was stirred at 25° C. for 5 hours. To the resulting mixture was added dropwise 48.3 g of water so that the internal temperature of the flask content was retained at 30° C. or lower, and this was liquid separation-treated. The resulting oil layer was washed with 85.0 g of water to perform liquid separation treatment, thereby, 83.7 g of the crude product of 2-chloromethylbenzaldehyde was obtained. A pH thereof exhibited about 1. When the crude product was analyzed by a high-performance liquid chromatography absolute calibration method, the content of 2-chloromethylbenzaldehyde was 88.7% by weight (A content ratio of 2CMAD [$\eta_{2CMAD}$] exceeded 99%). This sample was called A. In addition, Example 2 corresponds to Example 1-3 concerning preparation of 2CMAD, and the above description re-explained the content thereof.

Yield: 87.3% (on 1-dichloromethyl-2-chloromethylbenzene basis) GC-MS: m/z 118 (base peak), 118, 154 ($M^+$), 156 ($M^+$+2).

According to the same method as that of preparation of the sample A, 2-chloromethylbenzaldehyde was synthesized, and 100 ppm of 2,6-bis(1,1-dimethylethyl)-4-methylphenol (abbreviated as BHT) was added thereto. A pH thereof was about 1. This sample is called B.

The step of preparing the sample A was repeated to synthesize 2-chloromethylbenzaldehyde, a pH was adjusted to 6 to 8 with 83.7 g of an aqueous disodium hydrogen phosphate solution (10% by weight), and liquid separation-treated, and 0.008 g (100 ppm relative to the crude product of 2-chloromethylbenzaldehyde) of BHT was added. This sample is called C.

[Stability Test of 2-chloromethylbenzaldehyde]

Each of the samples A, B and C was observed with time at 20° C. by changing the presence or absence of oxygen, and the presence or absence of the stabilizer.

TABLE 2

| Preservation | | | | HPLC entire area % | |
|---|---|---|---|---|---|
| BHT | state | Sample | | 2CMAD | Phthalide |
| None | Air | Sample A (pH1) | Before test | 96.4 | 0 |
| | | | After 24 h | 88.3 | 8.1 |
| | | | After 48 h | 82.2 | 14.8 |
| | | | After 72 h | 78.4 | 17.7 |
| None | Nitrogen | Sample A (pH1) | Before test | 96.4 | 0 |
| | | | After 24 h | 96.4 | 0 |
| | | | After 48 h | 97.8 | 0.3 |
| | | | After 72 h | 96.5 | 0.4 |
| 100 ppm | Air | Sample B (pH1) | Before test | 96.4 | 0 |
| | | | After 24 h | 93.2 | 3.0 |
| | | | After 48 h | 91.5 | 5.6 |
| | | | After 72 h | 89.8 | 7.5 |
| 100 ppm | Nitrogen | Sample B (pH1) | Before test | 96.8 | 0 |
| | | | After 24 h | 96.7 | 0 |
| | | | After 48 h | 96.7 | 0 |
| | | | After 72 h | 96.7 | 0 |

2CMAD: 2-chloromethylbenzaldehyde

An analysis value is HPLC entire area %.

In addition, the stability result of the sample when BHT was 500 ppm in air remained to be unchanged from 100 ppm.

From the result of Table 2, it is seen that a sample using a particular stabilizer sample (B) exhibits high stability even under air preservation, and is an industrially useful high purity liquid composition.

In order to confirm influence of a pH, a sample with 100 ppm of BHT added thereto was preserved under nitrogen atmosphere. The result is shown in the following Table 3.

TABLE 3

| | | | | Content %* | |
|---|---|---|---|---|---|
| Temperature condition ° C. | Sample | pH of sample | Mass % before test | After 1 week | After 2 weeks |
| 20 | Sample B | 1 | 90.3 | 90.1% | 82.0% |
| | Sample C | 7-8 | 89.7 | 90.7% | 88.6% |
| 5 | Sample B | 1 | 90.3 | 89.8% | 84.8% |
| | Sample C | 7-8 | 89.7 | 91.5% | 91.5% |

*The content was calculated by an absolute calibration method of 2CMAD.

From the result of the above Table 3, it is seen that the liquid composition whose pH has been adjusted to a neutral region has further enhanced preservation stability. In addition, a pH was measured at room temperature (about 25° C.) using a pH meter EcoScan pH 5 manufactured by Nikko Hansen & Co., Ltd.

INDUSTRIAL APPLICABILITY

It is known that 2-chloromethylbenzaldehyde is useful as an intermediate of medicaments and electronic materials. The present invention can be industrially utilized as a new process for producing a 2-chloromethylbenzaldehyde compound or the like.

The invention claimed is:

1. A process for producing 2-chloromethylbenzaldehyde comprising:
    step (A) of mixing 1-dichloromethyl-2-chloromethylbenzene and sulfuric acid having a concentration of 84.5% by weight or more; and
    step (B) of mixing a mixture obtained in step (A) and water, and further comprising a step of mixing the resulting 2-chloromethylbenzaldehyde with at least one selected from the group consisting of a polymerization inhibitor and an antioxidant.

2. The process according to claim 1, wherein the at least one selected from the group consisting of a polymerization inhibitor and an antioxidant is at least one selected from the group consisting of 2,6-bis(1,1-dimethylethyl)-4-methylphenol (BHT), hydroquinone, monomethyl hydroquinone and phenothiazine.

3. A composition comprising 2-chloromethylbenzaldehyde and at least one selected from the group consisting of a polymerization inhibitor and an antioxidant.

4. The composition according to claim 3, wherein the at least one selected from the group consisting of a polymerization inhibitor and an antioxidant is at least one selected from the group consisting of 2,6-bis(1,1-dimethylethyl)-4-methylphenol (BHT), hydroquinone, monomethyl hydroquinone and phenothiazine.

5. The composition according to claim 3, further comprising 1-dichloromethyl-2-chloromethylbenzene, wherein a content ratio of a molar quantity of 2-chloromethylbenzaldehyde $[M_{2CMAD}]$ defined by the relationship with a molar quantity of 1-dichloromethyl-2-chloromethylbenzene $[M_{TCOX}]$ ($[\eta_{2CMAD}]=[M_{2CMAD}]/([M_{2CMAD}]+[M_{TCOX}])$) is 95% or more.

6. A method for storing a composition comprising storing the composition as defined in claim 3 under nitrogen atmosphere.

7. A process for producing 2-chloromethylbenzaldehyde comprising:
    step (A) of mixing 1-dichloromethyl-2-chloromethylbenzene and sulfuric acid having a concentration of 84.5% by weight or more; and
    step (B) of mixing a mixture obtained in step (A) and water, wherein an organic phase of the mixture obtained in step (B) is neutralized while controlling the liquid at pH 6 to 8.

8. The process according to claim 7, further comprising a step of mixing the resulting 2-chloromethylbenzaldehyde with at least one selected from the group consisting of a polymerization inhibitor and an antioxidant.

9. The process according to claim 7, wherein the at least one selected from the group consisting of a polymerization inhibitor and an antioxidant is at least one selected from the group consisting of 2,6-bis(1,1-dimethylethyl)-4-methylphenol (BHT), hydroquinone, monomethyl hydroquinone and phenothiazine.

10. The process according to claim 7, wherein sulfuric acid having a concentration of 84.5% by weight or more in step (A) contains water at 0.4 mol or more based on 1 mol of 1-dichloromethyl-2-chloromethylbenzene.

* * * * *